(12) United States Patent
Bailey et al.

(10) Patent No.: US 10,068,326 B2
(45) Date of Patent: Sep. 4, 2018

(54) SYSTEM AND METHOD FOR ENHANCING VISUAL INSPECTION OF AN OBJECT

(71) Applicant: Siemens Energy, Inc., Orlando, FL (US)

(72) Inventors: Kevin P. Bailey, Chuluota, FL (US); Ziyan Wu, Plainsboro, NJ (US); Jan Ernst, Plainsboro, NJ (US); Terrence Chen, Princeton, NJ (US); Birgi Tamersoy, Erlangen (DE)

(73) Assignee: SIEMENS ENERGY, INC., Orlando, FL (US)

( * ) Notice: Subject to any disclaimer, the term of this patent is extended or adjusted under 35 U.S.C. 154(b) by 224 days.

(21) Appl. No.: 15/073,819

(22) Filed: Mar. 18, 2016

(65) Prior Publication Data

US 2017/0270651 A1 Sep. 21, 2017

(51) Int. Cl.
*G06K 9/00* (2006.01)
*G06T 7/00* (2017.01)
*H04N 5/225* (2006.01)
*G01N 21/88* (2006.01)

(52) U.S. Cl.
CPC ......... *G06T 7/001* (2013.01); *G01N 21/8806* (2013.01); *H04N 5/2256* (2013.01); *G01N 2201/062* (2013.01); *G06T 2207/10152* (2013.01)

(58) Field of Classification Search
CPC ... G06T 7/001; H04N 5/2256; G01N 21/8806
See application file for complete search history.

(56) References Cited

U.S. PATENT DOCUMENTS

| 6,022,124 A * | 2/2000 | Bourn | G01N 21/8806 362/231 |
|---|---|---|---|
| 6,965,120 B1 * | 11/2005 | Beyerer | G01N 21/8806 250/559.39 |
| 7,039,228 B1 * | 5/2006 | Pattikonda | G01B 11/0608 348/87 |
| 7,099,002 B2 * | 8/2006 | Ishiura | G01N 21/8901 356/237.2 |
| 7,372,557 B2 * | 5/2008 | Oomori | G01N 21/9501 356/237.1 |
| 7,671,980 B2 * | 3/2010 | Matsui | G01N 21/8806 356/237.2 |
| 8,547,546 B2 * | 10/2013 | Suzuki | G01N 21/93 356/237.4 |

(Continued)

*Primary Examiner* — Gregory M Desire

(57) ABSTRACT

A method for inspecting an object to assist in determining whether the object has a surface defect. The method includes moving the object in a first direction and illuminating the object under ambient lighting conditions. The method also includes capturing at least one image of the object under the ambient lighting conditions while the object moves in the first direction. In addition, the object is illuminated under object lighting conditions and at least one image of the object under the object lighting conditions is captured while the object moves in the first direction to provide at least one object image. Further, the method includes selecting at least one object image having at least one indication of a possible defect to provide images having defect candidates and comparing the defect candidates with previously defined characteristics associated with the defect to facilitate determination of whether a defect exists.

18 Claims, 6 Drawing Sheets

FIG. 1

(56) References Cited

U.S. PATENT DOCUMENTS

| | | | |
|---|---|---|---|
| 9,136,186 B2* | 9/2015 | Yang | H01L 21/67288 |
| 2005/0046739 A1* | 3/2005 | Voss | H04N 5/2354 |
| | | | 348/371 |
| 2010/0004875 A1* | 1/2010 | Urano | G01N 21/4738 |
| | | | 702/40 |
| 2012/0147363 A1* | 6/2012 | Suzuki | G01N 21/93 |
| | | | 356/237.2 |
| 2013/0224963 A1* | 8/2013 | Hatano | G03F 7/0002 |
| | | | 438/758 |
| 2017/0270651 A1* | 9/2017 | Bailey | G06T 7/001 |
| 2017/0307544 A1* | 10/2017 | Nagata | G01N 21/95 |

* cited by examiner

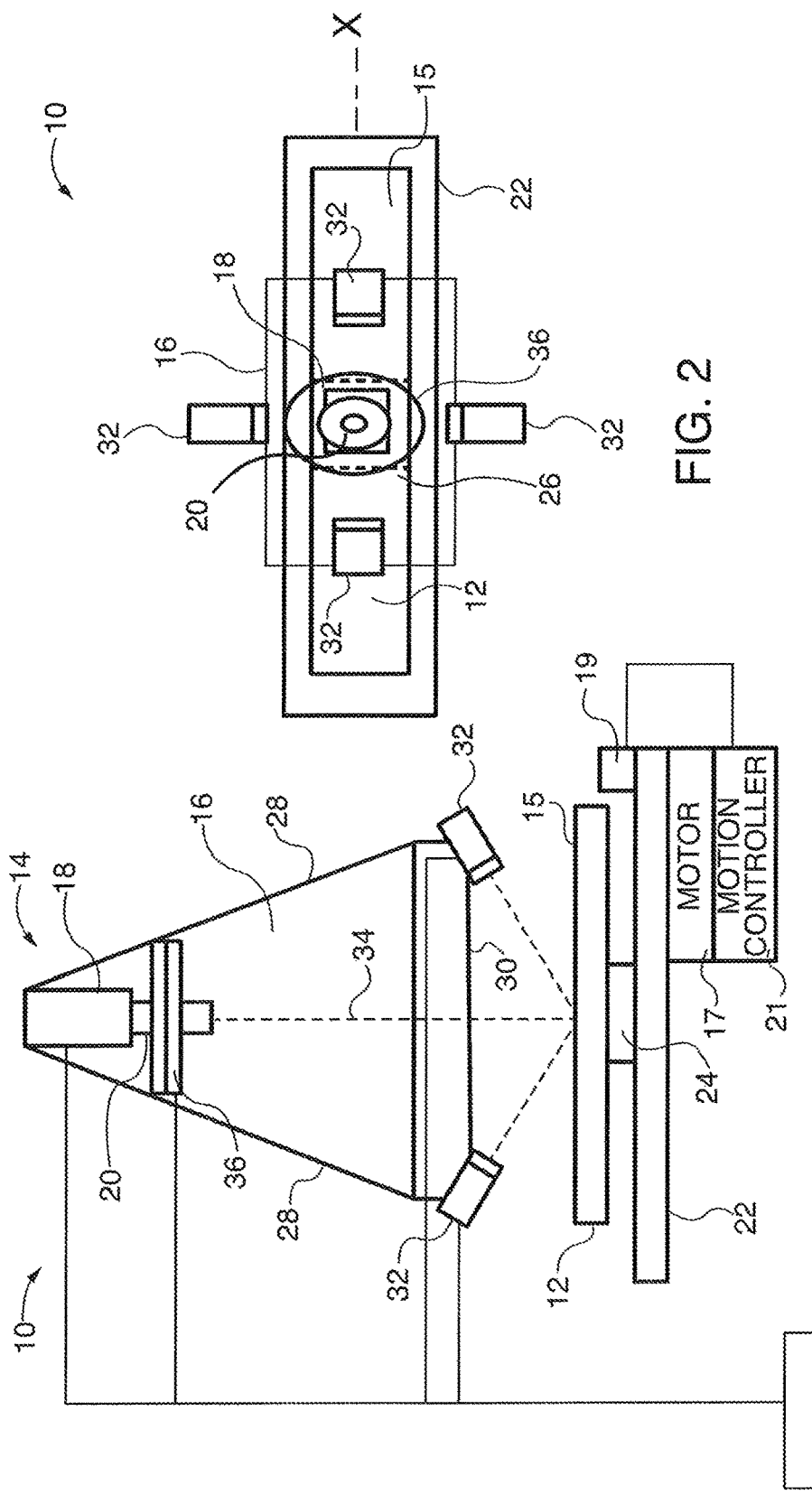

SYSTEM AND METHOD FOR ENHANCING VISUAL INSPECTION OF AN OBJECT

FIELD OF THE INVENTION

This invention relates to inspection systems, and more particularly, to a method for inspecting an object to assist in determining whether the object has a surface defect by comparing defect candidates in images captured under varied lighting conditions with previously defined characteristics associated with the defect to facilitate determination of whether a defect exists.

BACKGROUND OF THE INVENTION

Inspection methods such as liquid penetrant, magnetic particle and eddy current inspection methods are frequently used to detect small flaws or defects (i.e. less than approximately 2 mm size) on the surface of a component. Many surface inspection methods utilize chemicals or complicated equipment in order to achieve a high probability of detection of such defects. However, such inspection methods are environmentally unfriendly and expensive. Further, such inspection methods are time consuming and require a substantial amount of operator training in order to effectively operate the inspection equipment. It is desirable to provide improved surface inspection techniques that overcome the drawbacks of current methods.

SUMMARY OF INVENTION

A method for inspecting an object to assist in determining whether the object has a surface defect is disclosed. The method includes moving the object in a first direction and illuminating the object under ambient lighting conditions. The method also includes capturing at least one image of the object under the ambient lighting conditions while the object moves in the first direction. In addition, the object is illuminated under object lighting conditions and at least one image of the object under the object lighting conditions is captured while the object moves in the first direction to provide at least one object image. Further, the method includes selecting at least one object image having at least one indication of a possible defect to provide images having defect candidates. The defect candidates in the images are then compared with previously defined characteristics associated with the defect to facilitate determination of whether a defect exists.

Those skilled in the art may apply the respective features of the present invention jointly or severally in any combination or sub-combination.

BRIEF DESCRIPTION OF DRAWINGS

The teachings of the present disclosure can be readily understood by considering the following detailed description in conjunction with the accompanying drawings, in which:

FIG. 1 is a side view system for performing automated visual inspection of a surface of an object.

FIG. 2 is a top view of the system shown in FIG. 1.

To facilitate understanding, identical reference numerals have been used, where possible, to designate identical elements that are common to the figures.

DETAILED DESCRIPTION

Figure 3B:
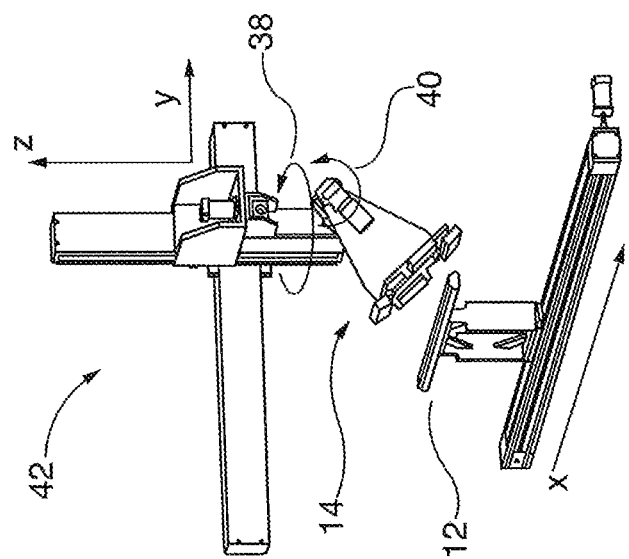
FIGS. 3A and 3B depict an overall motion platform for the system.

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

The current invention may be used to inspect objects such as generator wedges used in electrical generators utilized in power generation equipment. It is desirable to enhance the ability to detect surface defects or flaws in a generator wedge, such as cracks or other imperfections, in order to enhance performance and service life of the generator wedge. It is understood that the current invention is not limited to inspecting generator wedges and may be used to inspect other types of components or objects to, for example, verify whether an object meets desired quality parameters and/or to measure process variability, provide process control and perform other tasks.

Referring to FIGS. 1 and 2, side and top views, respectively, are shown of a system 10 for performing automated visual inspection of a surface 15 of an object 12. The system 10 includes an optical sensor 14 located inside a sensor hood 16. The optical sensor 14 includes an imaging device 18, such as a camera, and a lens 20. The system 10 also includes a linear stage 22 having a platform 24 that supports the object 12. The linear stage 22 is moved along a longitudinal X-axis by a motor 17 controlled by a motion controller 21. Information regarding a position of the linear stage 22 along the X-axis is provided to the motion controller 21 by an encoder 19.

The lens 20 and object 12 are spaced apart to provide a suitable field of view 26 for imaging the object 12. The hood 16 includes tapered surfaces 28 that taper away from each other and extend toward the object 12. A bottom portion 30 of the hood 16 includes at least one object illumination source 32 such as a light emitting diode ("LED") strobe light. For purposes of illustration, four object illumination sources 32 are shown in FIG. 2 although it is understood that additional or fewer object illumination sources 32 may be used. Each object illumination source 32 is oriented at a relatively large zenith angle relative to a vertical axis 34 of the object 12 suitable for providing dark field illumination of the object 12. In dark field illumination, for example, a first portion of a defect on the object 12 may form a bright region whereas a second portion of the defect is not illuminated thus forming a dark or shadow region. The bright and shadow regions are in the field of view 26 of the optical sensor 14. Further, light that impinges on a flat surface (i.e. a surface that does not include a defect) is reflected out of the field of view 26 of the optical sensor 14.

In addition, the system 10 includes at least one ambient illumination source 36 located inside the hood 16. The ambient illumination source 36 may be an LED strobe light having a ring shape ("LED ring light"). In an embodiment, the lens 20 extends through the ring light. Operation of the optical sensor 14, the ambient illumination source 36 and object illumination sources 32 is controlled by a trigger control module 54. The trigger control module 54 triggers the optical sensor 14, ambient illumination source 36 and object illumination sources 32 to capture images of the object 12 under selected lighting conditions as the object 12 is moved along the X-axis by the linear stage 22 to provide an automated inspection system.

Figure 3A:
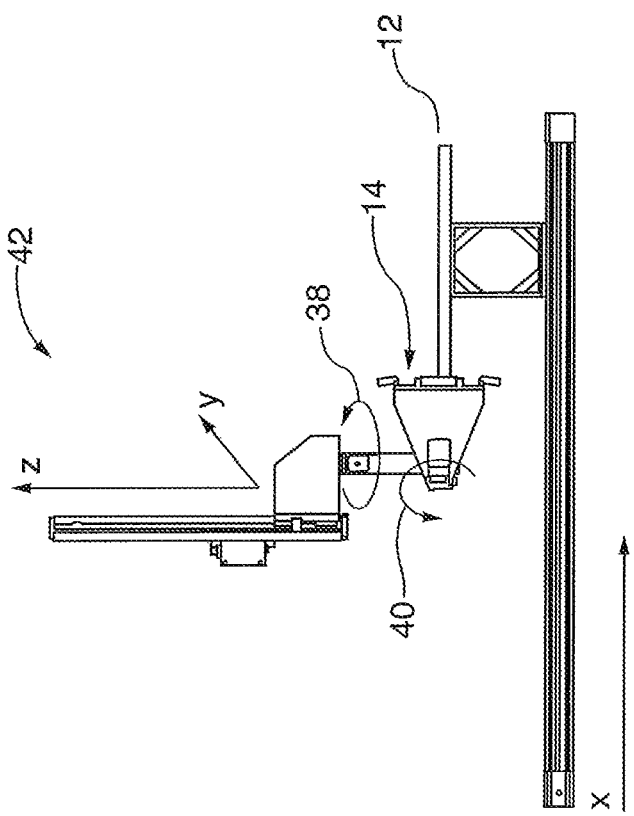

A relative position of the ambient illumination source 36 and object illumination sources 32 is adjustable to provide a plurality of tilt angles suitable for illuminating the object 12. Further, a position of the optical sensor 14 may be adjustable. A position of each object illumination source 32 and/or optical sensor 14 is fixed after suitable illumination parameters are obtained during an illumination calibration procedure. FIGS. 3A and 3B depict an overall motion platform 42 for the system 10. The motion platform 42 includes X, Y, Z axes in a Cartesian coordinate system and pan 38 and tilt 40 angles in a spherical coordinate system used to adjust a pointing direction of the optical sensor 14 relative to the object 12. In addition, the linear stage 22 moves the object 12 along the X axis.

Figure 4A:
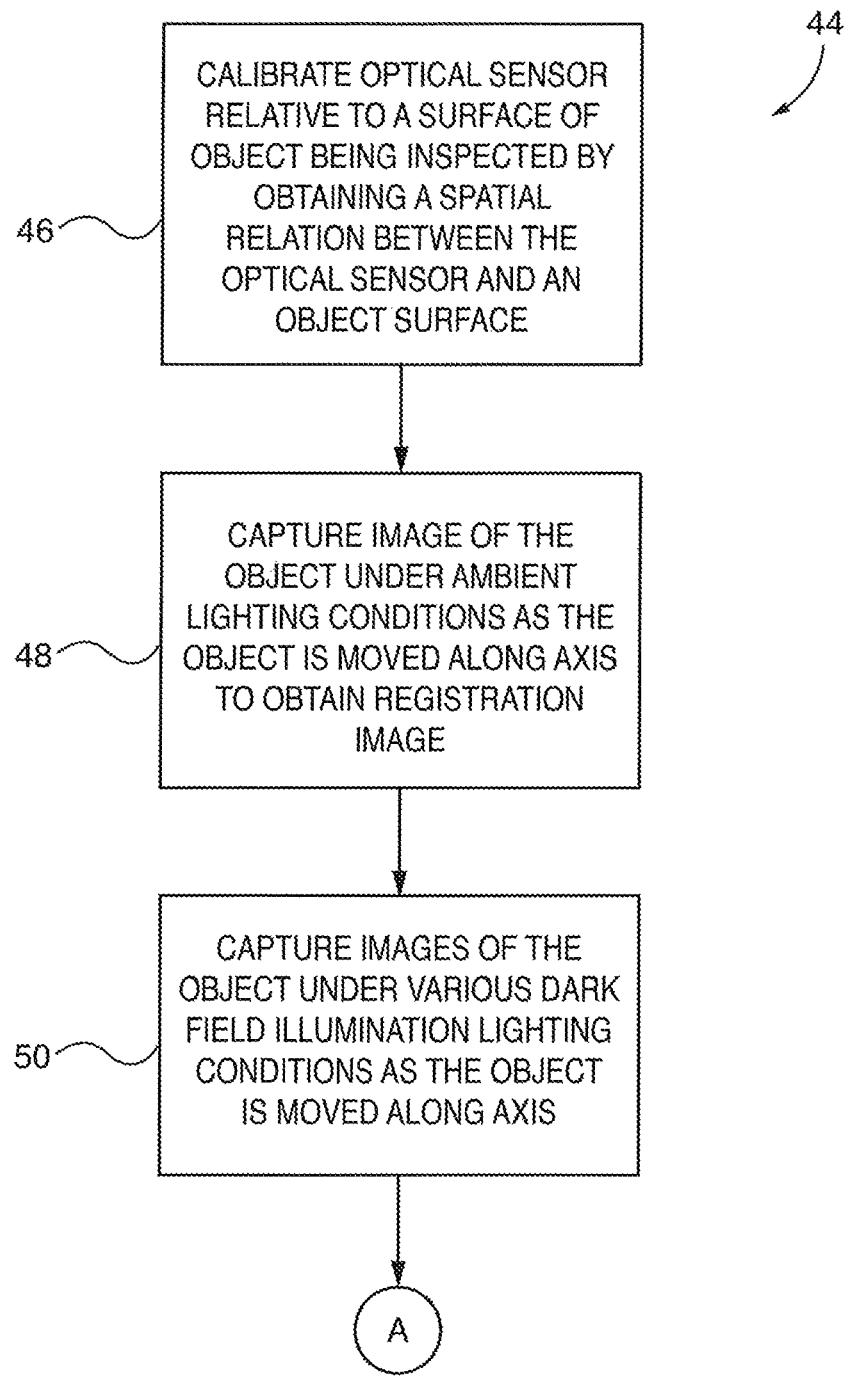
FIGS. 4A-4B depict a method for detecting surface defects in accordance with an aspect of the current invention.
Figure 4B:
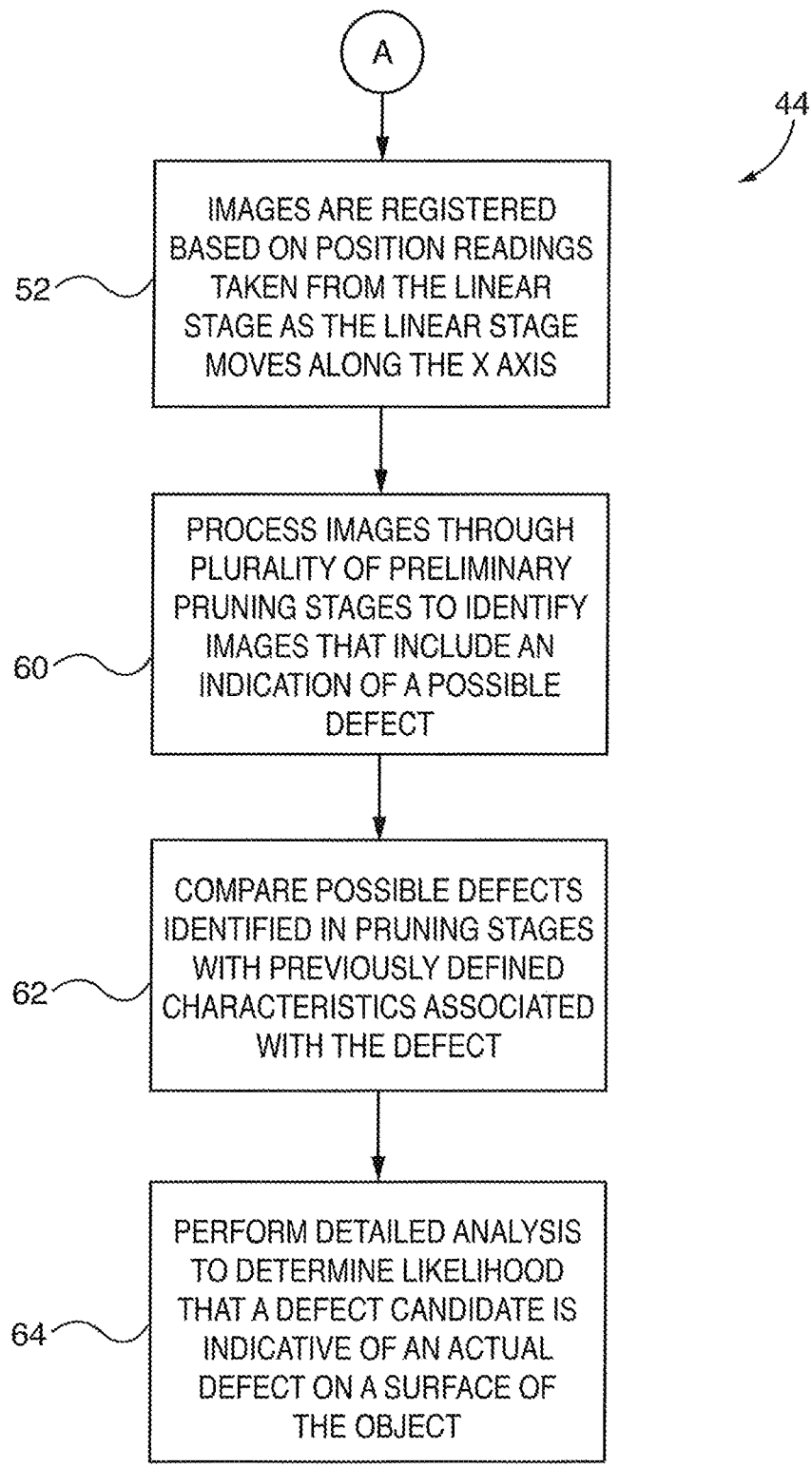

Referring to FIGS. 4A-4B, a method 44 for detecting surface defects will now be described. At step 46, the optical sensor 14 is calibrated relative to a surface 15, or working plane, of the object 12 being inspected by capturing a spatial relation between the optical sensor 14 and surface 15. At step 48, the ambient illumination source 36 is turned on to capture a registration image of the surface 15 under ambient lighting conditions as the object 12 is moved along the X-axis by the linear stage 22. The optical sensor 14 is then activated to capture images of the object 12 under various dark field illumination conditions as the object 12 is moved along the X-axis by the linear stage 22 at step 50. For example, the object illumination sources 32 may be turned on and off in a desired sequence, pattern, simultaneously, with varied lighting levels etc. as the object 12 is moved by the linear stage 22 during image capture. At step 52, the images captured under ambient and dark field lighting conditions are registered based on position readings taken from the linear stage 22 as the linear stage 22 moves along the X-axis. For purposes of registration, it is assumed that the object 12 is undergoing pure translation movement during registration. Thus, accurate registration is obtained between images obtained under different illumination configurations and their corresponding spatial positions.

At step 60, the images are processed through a plurality of preliminary pruning stages that identify images which include an indication of a possible defect such as a crack. Images that do not have the indication are then ruled out. For example, in a first pruning stage, the images are screened to identify images that include a characteristic indicative of dark field illumination, such as a bright or shadow region, and thus the existence of a possible defect. Remaining images that do not include a characteristic indicative of dark field illumination are ruled out so that no further processing is undertaken for the ruled out images. In a second pruning stage, the images identified in the first pruning stage are again screened to identify whether the images include an indication of an additional or alternative characteristic indicative of a possible defect. For example, each image in the second pruning stage may be compared to the registration image to determine whether any differences between the registration image and an image being screened are indicative of a possible defect. It is understood that additional pruning stages may be used. Alternatively, a single preliminary pruning stage may be used.

At the conclusion of the preliminary pruning stages, a plurality of screened images remains each including possible defect candidates. At step 62, the possible defects identified in the screened images are then compared with previously defined characteristics associated with the defect. In an embodiment, the characteristics may be based on previous observations of the defect under varied lighting conditions that have been noted and compiled by the inventors herein. In the case of a defect such as a crack, the characteristics may include crack length, width, thickness, orientation and other characteristics under various illumination conditions.

At step 64, a detailed analysis is then performed by trained personnel to determine the likelihood that a defect candidate is an actual defect on a surface of the object. The determination is based on a comparison of a defect candidate with the predetermined crack characteristics, illumination configuration for the image, camera intrinsic and extrinsic parameters and other factors.

Figure 5:
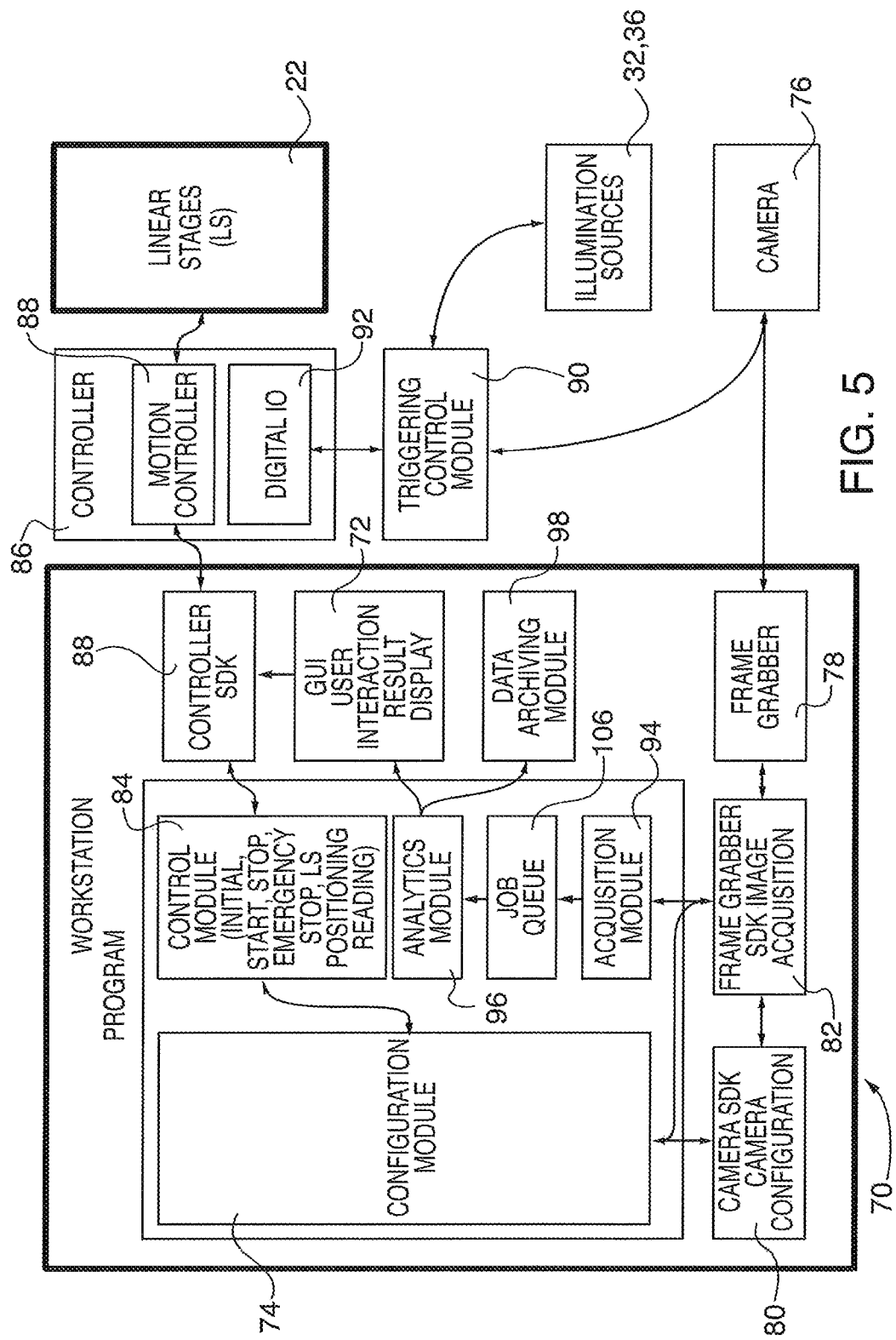
FIG. 5 depicts a software and input/output (I/O) architecture in accordance with the present invention.

Referring to FIG. 5, software and input/output (I/O) architecture 70 in accordance with the present invention is shown. The architecture 70 enables simultaneous image acquisition and processing in order to satisfy challenging time constraints. The architecture 70 includes a plurality of modules including a user interface module or graphical user interface ("GUI") 72 that enables user interaction and provides a result display. The architecture also includes a Configuration Module 74 for setting parameters for software and hardware. This includes configuring an optical sensor such as a Camera 76 and a Frame Grabber 78 via a Camera Software Development Kit ("SDK") 80 and a Frame Grabber SDK 82 which include camera and frame grabber libraries, respectively, that enable configuration and image acquisition. In addition, architecture 70 includes a Control Module 84 for sending commands and instructions such as initial, start, stop, emergency stop, linear stage position reading and others to a Controller 86 via a Controller SDK 88 that provides access to a controller library and serves as an interface. The Controller 86 controls a Motion Controller 88 that controls movement of the linear stage 22 so that the object 12 is moved in a continuous motion. The Controller 88 also controls a Triggering Control Module 90 via a Digital I/O device 92. The Triggering Control Module 90 triggers the object 32 and ambient 36 illumination sources and the camera 76 to capture images of the object 12 under various lighting conditions as previously described. Further, the architecture 70 includes an Acquisition Module 94 that fetches images from the camera 76 and an Analytics Module 96 for processing and analyzing images received from a job queue 106 including batches of images to assist trained personnel in determining whether the object 12 under inspection has defects. Data generated by the Analytics Module 96 may then be archived in a Data Archiving Module 98.

Figures 6, 7:
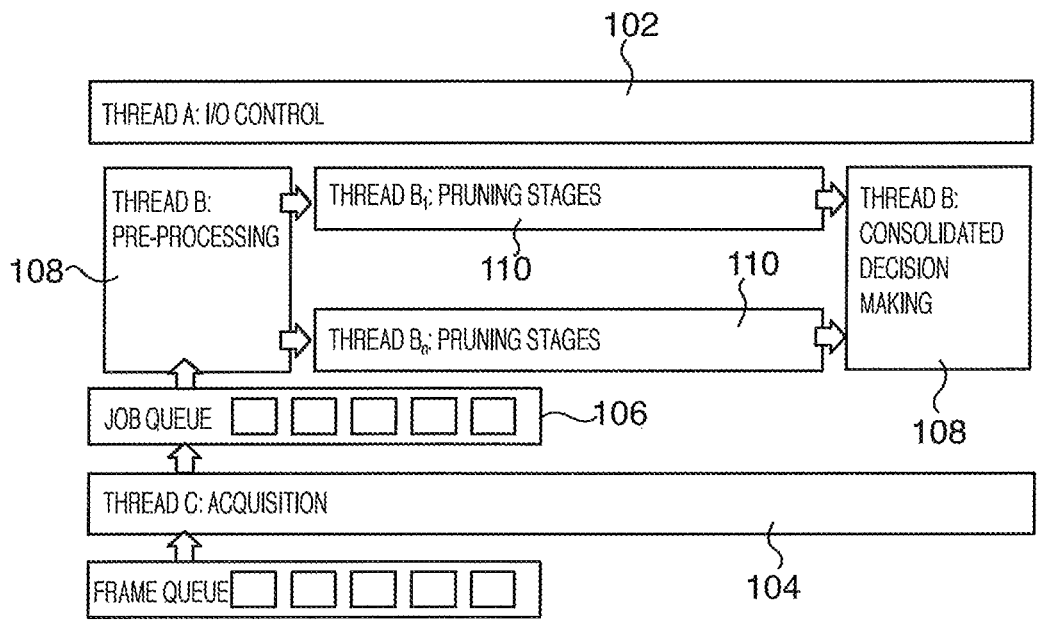
FIG. 6 depicts software architecture for providing a parallel processing mechanism for a scanning process in accordance with the current invention.
FIG. 7 depicts a sample inspection report.

Referring to FIG. 6, software architecture 100 for providing a parallel processing mechanism for the scanning process is shown. The architecture 100 includes a plurality of software threads. In particular, Thread A 102 is used to control I/Os, e.g. sending commands and instructions to the Motion Controller 88. Thread C 104 handles image acquisition and sends captured images to the job queue 106 for analytics processing. The images are preprocessed in Thread B 108 before the images are divided into small batches. The images are then sent to multiple analytics threads ($B_1 \ldots B_n$) 110 for multi-stage pruning as previously described. Further, Thread B 108 collects decisions from the analytics threads and generates a consolidated decision regarding defects that is then reviewed by trained personnel.

After each object 12 is scanned, a trained operator determines whether a defect exists on an object 12 and an inspection report is subsequently generated. Referring to FIG. 7, a sample inspection report 112 is shown. The inspection report 112 includes information such as an identification number 114 for each defect, corresponding batch number 116, date 118, time 120, surface inspected 122 and X and Y position 124 of the defect on the surface 15.

The system of the present invention may be configured as a portable device to enable remote inspection of objects. Further, the system does not utilize environmentally unfriendly materials used in conventional methods and requires very little technical training for an inspector. It has been found by the inventors herein that the system has a higher flaw detection capability, faster inspection speed and lower cost when compared to current inspection methods. In addition, the system may be used for nondestructive evaluation ("NDE") inspection of generator wedges, machined parts and other components.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method for inspecting an object to assist in determining whether the object has a surface defect, comprising:
   moving the object in a first direction by a linear stage;
   illuminating the object under ambient lighting conditions by at least one ambient illumination source;
   capturing at least one image of the object under the ambient lighting conditions while the object moves in the first direction to provide a registration image by an optical sensor;
   illuminating the object under object lighting conditions by at least one object illumination source;
   capturing at least one image of the object under the object lighting conditions while the object moves in the first direction to provide at least one object image by the optical sensor;
   selecting at least one object image having at least one indication of a possible defect to provide images having defect candidates by a controller;
   comparing the defect candidates with previously defined characteristics associated with the defect to facilitate determination of whether a defect exists by the controller,
   the method further comprising registering the registration image captured under the ambient lighting conditions with the at least one image of the object captured under the object lighting conditions based on position readings from the linear stage by the controller.

2. The method according to claim 1, wherein an indication of a possible defect includes determining whether the at least one object image has a bright or a shadow region.

3. The method according to claim 1, wherein an indication of a possible defect includes comparing the object image with the registration image.

4. The method according to claim 1, wherein a plurality of pruning stages are used to select the at least one object image.

5. The method according to claim 1, wherein the previously defined characteristics include length, width, thickness, orientation of a crack.

6. The method according to claim 1, wherein illuminating the object under object lighting conditions includes operating a plurality of object illumination sources in accordance with a desired sequence or operating the object illumination sources simultaneously to provide the object lighting conditions.

7. A method for inspecting an object to assist in determining whether the object has a surface defect, comprising:
   providing a linear stage to move the object in a first direction;
   operating at least one ambient illumination source to illuminate the object under ambient lighting conditions;
   providing an optical sensor to capture at least one image of the object under the ambient lighting conditions while the object moves in the first direction to provide a registration image;
   operating at least one object illumination source to illuminate the object under object lighting conditions;
   operating the optical sensor to capture at least one image of the object under the object lighting conditions while the object moves in the first direction to provide at least one object image;
   selecting at least one object image having at least one indication of a possible defect to provide images having defect candidates by a controller;
   comparing the defect candidates with previously defined characteristics associated with the defect to facilitate determination of whether a defect exists by the controller,
   the method further comprising registering the registration image captured under the ambient lighting conditions with the at least one image of the object captured under the object lighting conditions based on position readings from the linear stage by the controller.

8. The method according to claim 7, wherein an indication of a possible defect includes determining whether the at least one object image has a bright or a shadow region.

9. The method according to claim 7, wherein an indication of a possible defect includes comparing the object image with the registration image.

10. The method according to claim 7, wherein a plurality of pruning stages are used to select the at least one object image.

11. The method according to claim 7, wherein the previously defined characteristics include length, width, thickness, orientation of a crack.

12. The method according to claim 7, wherein illuminating the object under object lighting conditions includes operating a plurality of object illumination sources in accordance with a desired sequence or operating the object illumination sources simultaneously to provide the object lighting conditions.

13. A system for inspecting an object to assist in determining whether the object has a surface defect, comprising:
- a linear stage for moving the object in a first direction;
- at least one ambient illumination source to illuminate the object under ambient lighting conditions;
- an optical sensor to capture at least one image of the object under the ambient lighting conditions;
- at least one object illumination source to illuminate the object under object lighting conditions; and
- a controller for controlling the optical sensor and the ambient and objection illumination sources,
- wherein the optical sensor captures at least one image of the object under the ambient lighting conditions to provide a registration image and at least one image of the object under the object lighting conditions while the object moves in the first direction,
- wherein the controller selects at least one object image having at least one indication of a possible defect to provide images having defect candidates,
- wherein the controller compares the defect candidates with previously defined characteristics associated with the defect to facilitate determination of whether a defect exists, and
- wherein the controller registers the registration image captured under the ambient lighting conditions with the at least one image of the object captured under the object lighting conditions based on position readings from the linear stage.

14. The system according to claim 13, wherein the ambient and object illumination sources are light emitting diode ("LED") strobe lights.

15. The system according to claim 14, wherein the ambient illumination source is an LED ring light.

16. The system according to claim 13, wherein an indication of a possible defect includes determining whether the at least one object image has a bright or a shadow region.

17. The system according to claim 13, wherein an indication of a possible defect includes comparing the object image with the registration image.

18. The system according to claim 13, wherein the previously defined characteristics include length, width, thickness, orientation of a crack.

* * * * *